(12) United States Patent
Choong et al.

(10) Patent No.: US 6,596,483 B1
(45) Date of Patent: Jul. 22, 2003

(54) SYSTEM AND METHOD FOR DETECTING MOLECULES USING AN ACTIVE PIXEL SENSOR

(75) Inventors: Vi-En Choong, Chandler, AZ (US); George N. Maracas, Phoenix, AZ (US)

(73) Assignee: Motorola, Inc., Schaumburg, IL (US)

( * ) Notice: Subject to any disclaimer, the term of this patent is extended or adjusted under 35 U.S.C. 154(b) by 0 days.

(21) Appl. No.: 09/440,031

(22) Filed: Nov. 12, 1999

(51) Int. Cl.[7] .......................... C12Q 1/68; C12P 19/34; C12M 1/34; C07H 21/02; C07H 21/04
(52) U.S. Cl. ..................... 435/6; 435/7.1; 435/91.1; 435/91.2; 435/287.2; 536/22.1; 536/23.1; 536/24.3; 536/24.31; 536/24.32; 536/24.33; 377/60; 250/306
(58) Field of Search .................... 435/6, 7.1, 91.1, 435/91.2, 287.2; 536/22.1, 23.1, 24.3–33

(56) References Cited

U.S. PATENT DOCUMENTS

| | | |
|---|---|---|
| 4,851,331 A | 7/1989 | Vary et al. |
| 5,471,515 A | 11/1995 | Fossum et al. |
| 5,585,639 A | 12/1996 | Dorsel et al. |
| 5,653,939 A | 8/1997 | Hollis et al. |
| 5,741,411 A * | 4/1998 | Yeung et al. ............... 204/452 |
| 5,841,126 A | 11/1998 | Fossum et al. |
| 5,846,708 A | 12/1998 | Hollis et al. |
| 5,851,772 A * | 12/1998 | Mirzabekov et al. .......... 435/6 |
| 5,863,504 A | 1/1999 | Heffelfinger et al. |
| 5,874,219 A | 2/1999 | Rava et al. |
| 5,885,531 A | 3/1999 | Heffelginer et al. |
| 5,888,819 A | 3/1999 | Goelet et al. |
| 5,922,617 A | 7/1999 | Wang et al. |
| 5,932,873 A * | 8/1999 | Bergemont et al. ....... 250/208.1 |
| 5,945,722 A | 8/1999 | Tsuei et al. |
| 5,981,956 A | 11/1999 | Stern |
| 5,991,030 A | 11/1999 | Yamamoto et al. |
| 6,325,977 B1 * | 12/2001 | Theil ...................... 422/82.05 |

FOREIGN PATENT DOCUMENTS

| | | |
|---|---|---|
| GB | 2 289 979 A | 12/1995 |
| JP | 11183437 A | 7/1999 |
| WO | WO 95/00669 A1 | 1/1995 |
| WO | WO 99/13109 | 3/1999 |
| WO | WO 99/57547 | 11/1999 |

OTHER PUBLICATIONS

Kheterpal, I., et al., DNA Sequencing using a Four–Color Confocal Fluorescence Capillary Array Scanner, *Electrophoresis*, 17: 1852–1859 (1996).
Motorola Inc., Motorola Semiconductor Technical Data for SCM200140 Image Sensor, dated Aug. 9, 1999.
NASA's Jet Propulsion Laboratory, "Active–Pixel–Sensor Digital Camera on a Single Chip", NASA Tech Briefs, p. 44–48 (Oct. 1998).
Orly Yadid–Pecht, Barmak Mansoorian, Eric R. Fossum and Bedabrata Pain, "Optimization of Noise and Responsivity in CMOS Active Pixel Sensors for Detection of Ultra Low Light Levels", Proceedings of SPIE, vol. 3019, p. 125–136 (Feb. 10–11, 1997).
Eric R. Fossum, "Novel Sensor Enables Low–Power, Miniaturized Imagers", Photonics Spectra, p. 125–126 (Jan., 1996).

* cited by examiner

Primary Examiner—Jeffrey Siew
(74) *Attorney, Agent, or Firm*—Robin M. Silva; Dorsey & Whitney LLP (57) ABSTRACT

In a molecule detection system and method, a sample containing target molecules is added to an array of test sites, with each test site containing distinct probe molecules. The probe molecules bind with the target molecules in the sample to form bound complexes. A source illuminates the array of test sites with incident electromagnetic radiation, and an active pixel sensor detects the electromagnetic radiation from the array. To detect the presence of target molecules in the sample, the active pixel sensor detects changes in the optical properties of the test sites that result, either directly or indirectly, from their binding of the probe molecules with the target molecules. The target molecules may also be characterized on the basis of which probe molecules bind to them.

27 Claims, 10 Drawing Sheets

SYSTEM AND METHOD FOR DETECTING MOLECULES USING AN ACTIVE PIXEL SENSOR

BACKGROUND OF THE INVENTION

1. Field of the Invention

This invention relates to the field of molecule detection. More particularly, this invention relates to a system and method for using an active pixel sensor to optically detect the binding of probe molecules to target molecules.

2. Description of Related Art

In many applications, it is desirable to detect the presence of one or more types of target molecules in a sample. For samples of biological interest, such target molecules may include antigens, antibodies, or nucleic acids. One method for detecting target molecules in a sample involves the use of probe molecules that bind to only specific types of target molecules that may be present in the sample to form bound complexes. For example, if antigens are to be detected, antibodies specific for those antigens can be used as the probe molecules. Similarly, antigens can serve as the probe molecules to detect the presence of antibodies to that antigen. Additionally, nucleic acids can be detected by probe molecules having a sequence of nucleotides that is complementary to at least a portion of the nucleotide sequence in the nucleic acid, so that the probe molecules will hybridize with the target nucleic acids.

In order to detect target molecules, the probe molecules are disposed in a test site, and the sample is added to the test site to allow the probe molecules to bind with any target molecules present in the sample. The binding of probe molecules with target molecules can then be detected in a number of different ways, such as by measuring changes in the electrical or optical characteristics of the test sites.

Optical detection is potentially a very useful technique and can be accomplished in various ways. One approach is to apply electromagnetic radiation at a given wavelength, typically in the infrared, visible, or ultra-violet spectra, at which the absorbance of the bound complexes is substantially different than that of the unbound probe molecules. This approach, however, has the disadvantage of potentially requiring different wavelengths to be used depending on the probe molecules used and the target molecules to be detected. This approach can also suffer from low sensitivity.

A potentially better approach is to label the target molecules in a sample with fluorescent dyes (described herein as "fluorophores") before the target molecules are exposed to the probe molecules. Such fluorophores emit fluorescence radiation in a characteristic range of wavelengths when exposed to electromagnetic radiation at a characteristic excitation wavelength. Thus, the probe molecules will bind with target molecules to form bound complexes that are fluorescent. Binding can then be detected by illuminating the test sites with electromagnetic radiation at the excitation wavelength and sensing whether the bound complexes in the test sites emit fluorescence radiation.

Alternatively, instead of labeling the target molecules in the sample, the bound complexes can be exposed to a selective dye after they are formed. Selective dyes are dyes that exhibit substantial changes in their optical properties in the presence of bound complexes. For example, ethidium bromide is a fluorescent dye that exhibits an approximate 20-fold increase in fluorescence when intercalated into hybridized nucleic acids, as compared to when the dyes is unbound or bound only to unhybridized nucleic acids. In this way, the binding of molecular probes can be detected as either a substantial increase in fluorescence or a substantial increase in absorbance at the excitation wavelength.

In many cases, it is known that target molecules are present in a sample, but the nature of the target molecules is unknown. The probe molecules can then serve not only to detect the presence of target molecules in a sample but also to determine what the target molecules are. For example, a sample containing nucleic acids having an unknown nucleotide sequence may be exposed to multiple sets of probe molecules, with each set having a different nucleotide sequence. In this way, the nucleotide sequence of the nucleic acids can be determined from detecting which probe molecules bind to it.

Hollis et al., U.S. Pat. No. 5,653,939 disclose an apparatus that uses a plurality of different types of probe molecules disposed in an array of test sites to identify target molecules in a sample. To allow for optical detection of binding, the apparatus includes a charge-coupled device (CCD), in which each pixel is aligned with a respective test site. In this way, a change in the optical characteristics of the probe molecules in a given test site, due to binding with target molecules, can detected by the corresponding pixel. The array of test sites can be fabricated on the same chip as the CCD, or it can be provided in a separate glass plate. Optical detection of binding can occur in any of the ways described above, namely: (1) increased light attenuation caused by probe molecules binding with target molecules; (2) increased light attenuation at the excitation wavelength or increased fluorescence caused by ethidium bromide selectively intercalating into hybridized DNA; or (3) detection of fluorescence radiation after the probe molecules have bound to fluorescently-labeled target molecules. To better detect fluorescence radiation, each CCD pixel may be provided with a filter designed to block the excitation radiation and pass the fluorescence radiation.

Although the apparatus of Hollis et al. may potentially allow for the rapid detection and characterization of target molecules using a plurality of probe molecules, many shortcomings remain. Chief among these is inadequate portability. In particular, it is desirable in many applications to have a molecular detection apparatus that is portable, so that it can be brought to the location where the samples are collected.

However, CCDs, which are used in the apparatus of Hollis et al., have a number of characteristics that make them difficult to use in a portable molecular detection apparatus. First, CCDs are typically fabricated using a specialized process that is incompatible with conventional complementary metal oxide semiconductor (CMOS) processing. As a result, it is impractical to integrate the electronics necessary for amplification and image signal processing (which are best fabricated in CMOS) on the same chip as the CCD. Accordingly, when CCDs are used, portability is hampered by the need to include extensive off-chip signal processing electronics. Second, portability is made difficult in that CCDs require relatively complicated power supplies. Specifically, CCDs typically require voltages at three different levels (such as +15V, −15V, and −8V) to operate. Third, CCDs and their associated electronics have a relatively high power dissipation. Fourth, CCDs are often cooled, such as by using fans, liquid nitrogen, or thermoelectrically. Accordingly, portability is further hindered by the need to provide additional cooling components that take up additional space, add weight, and increase costs. Moreover, the cooling components themselves require a substantial amount of power to operate, and they typically have their own power supplies, thereby further increasing the size and weight of the apparatus needed when using CCDs. CCDs are cooled for a number of different reasons. An important reason for cooling CCDs is to reduce noise, which is temperature dependent. Low noise operation allows CCDs to detect very weak signals. Notably, the ability to detect very weak signals is essential for molecule detection in biological samples, because only 1 femtomole or less of target molecules may be bound in a given test site. Thus, cooling is often needed in applications, such as molecule detection, where the CCD must be able to detect very weak signals. Additionally, because of the power dissipation in the CCD and associated electronics, cooling is often necessary to prevent damage to the components. Fifth, CCDs have another important limitation in that they read each pixel by transferring the photo-generated charge pixel by pixel until it reaches an amplifier at the edge of the device. Thus, a high charge transfer efficiency (CTE) is essential for good sensitivity in CCDs. Because the CTE decreases with increasing temperature, cooling is often required for good sensitivity. Sixth, to control exposure times of CCDs, external mechanical shutters are used. Such mechanical shutters take up space and require power to operate, thereby further hampering portability. Thus, it is difficult to make a CCD-based molecule detection apparatus highly portable because of the need to provide extensive electronics, complicated power supplies, cooling components, and an external mechanical shutter that take up a substantial amount space and require a substantial amount of power to operate.

In addition to poor portability, CCDs suffer from a phenomenon called "blooming." Blooming occurs when a very strong signal saturates one pixel and causes charge to leak into neighboring pixels, thereby resulting in anomalous readings in the neighboring pixels. This can be a major problem when an array of test sites is used, because one test site may produce a very strong signal (e.g., because of probe molecules binding with fluorescently-labeled target molecules), whereas neighboring test sites may not have any binding and, thus, produce little or no signal. Accordingly, blooming from the strong signal may result in false positive readings in the neighboring pixels.

Finally, CCDs can also be substantially expensive because of the specialized techniques used to fabricate them.

Accordingly, a need exists to provide a molecular detection apparatus that allows rapid detection with high sensitivity and that is also portable.

SUMMARY OF THE INVENTION

In a first principal aspect, the present invention provides a system for testing a sample for the presence of target molecules. The system comprises a test site for receiving the sample, a source system for providing incident electromagnetic radiation, including radiation at a first wavelength, which radiation is directed to the test site, and an active pixel sensor. The active pixel sensor has a plurality of pixels, at least one of which is disposed for detecting electromagnetic radiation from the test site.

In a second principal aspect, the present invention provides a method for testing a sample for the presence of target molecules. The sample is added to a test site containing probe molecules that are able to bind to the target molecules to form bound complexes. The test site is illuminated with electromagnetic radiation, including radiation at a first wavelength. The electromagnetic radiation from the test site is detected with at least one pixel of an active pixel sensor.

In a third principal aspect, the present invention provides a method for identifying an unknown nucleotide in a nucleic acid, using a system comprising an active pixel sensor. The nucleic acid is added to a test site containing probe molecules that are able to hybridize with a nucleotide sequence adjacent to the unknown nucleotide in the nucleic acid. First, second, third, and fourth reporter molecules are added to the test site. The four types of reporter molecules comprise adenine, cytosine, guanine, and thymine conjugated to first, second, third, and fourth fluorophores, respectively. Each of the four fluorphores emits fluorescence radiation at a certain wavelength when exposed to electromagnetic radiation at a certain excitation wavelength. The test site is illuminated with electromagnetic radiation at each of the four excitation wavelengths in succession, and, during each such illumination period, a successive pixel of the active pixel sensor detects electromagnetic radiation from the test site.

In a fourth principal aspect, the present invention provides an improvement to a system for optically detecting the presence of specified molecules at specified locations. The improvement comprises an active pixel having a plurality of pixels. At least one of the pixels is disposed for detecting electromagnetic radiation from one of the specified locations.

In a fifth principal aspect, the present invention provides a method for monitoring the population of specified molecules at a location as a function of time. During a first time interval, at least one pixel of an active pixel sensor detects electromagnetic radiation from the location to obtain a first measurement. During a second time interval, the pixel detects electromagnetic radiation from the location to obtain a second measurement. The first and second measurements are then compared.

DETAILED DESCRIPTION OF THE INVENTION

Active pixel sensors are imaging devices characterized by having a plurality of pixels, wherein a light-sensitive element and one or more active devices, such as for readout, are integrated in each pixel. Active pixel sensors are typically made using conventional CMOS processes in order to facilitate the on-chip integration of image processing electronics with light-sensitive elements. Further details regarding the architecture of active pixel sensors are provided by U.S. Pat. Nos. 5,471,515 and 5,841,126, which are fully incorporated herein by reference.

The characteristics of active pixel sensors differ markedly from those of CCDs in a number of important respects. First, because the image processing electronics are integrated with the light-sensitive elements in an active pixel sensor, the need for external circuitry is greatly reduced. Second, in an active pixel sensor, the photo-generated charge in each pixel is read out directly, rather than being transferred pixel by pixel, so that these devices are much less subject to the temperature-dependent CTE that CCDs have. This reduces the need for cooling in an active pixel sensor, thereby saving eliminating the space and power requirements that would be otherwise needed for cooling components. Third, active pixel sensors typically dissipate only 1% to 10% of the power dissipated by CCDs. This reduces the size of the power supply needed and, because less heat is generated, further reduces the need for cooling. Fourth, active pixel sensors can operate when supplied with only a single voltage, thereby further simplifying the required power supply. Fifth, active pixel sensors can be electronically shuttered, whereby the pixel exposure time is controlled electronically. This has the advantage of obviating the need for external mechanical shutters that are used with CCDs. All of these advantages make active pixel sensors much more suited for portable systems than CCDs. Additionally, active pixel sensors do not have the blooming problem that plagues most CCDs. This is an important advantage in molecule detection systems. Finally, active pixel sensors can be fabricated more inexpensively than CCDs.

On the other hand, active pixel sensors have two important disadvantages as compared to CCDs. First, active pixel sensors have a lower "fill factor" than CCDs. "Fill factor" is the ratio of the area of the pixel that is light-sensitive to the total pixel area. Most CCDs have fill factors between 80 to 100%. However, because each pixel in an active pixel sensor includes active components as well as light-sensitive components, active pixel sensors typically have fill factors between 35 to 50%. Thus, an active pixel sensor will collect fewer photons than a CCD for the same light level. Second, active pixel sensors suffer from "fixed pattern noise," which limits their ability to detect very weak signals. Fixed pattern noise is typically due to differences in each pixel's amplification. In particular, fixed pattern noise arises in active pixel sensors because each pixel has its own amplifier, and variations in the characteristics of each amplifier are unavoidable. Together, these two problems can make active pixel sensors difficult to use in low light applications, such as molecule detection systems. Despite these potential problems, by reducing fixed pattern noise and by providing a spatially concentrated signal from the probe molecules, as described herein, uncooled active pixel sensors have been shown to be able to detect less than 1 femtomole of target molecules in a given test site.

Figure 1:
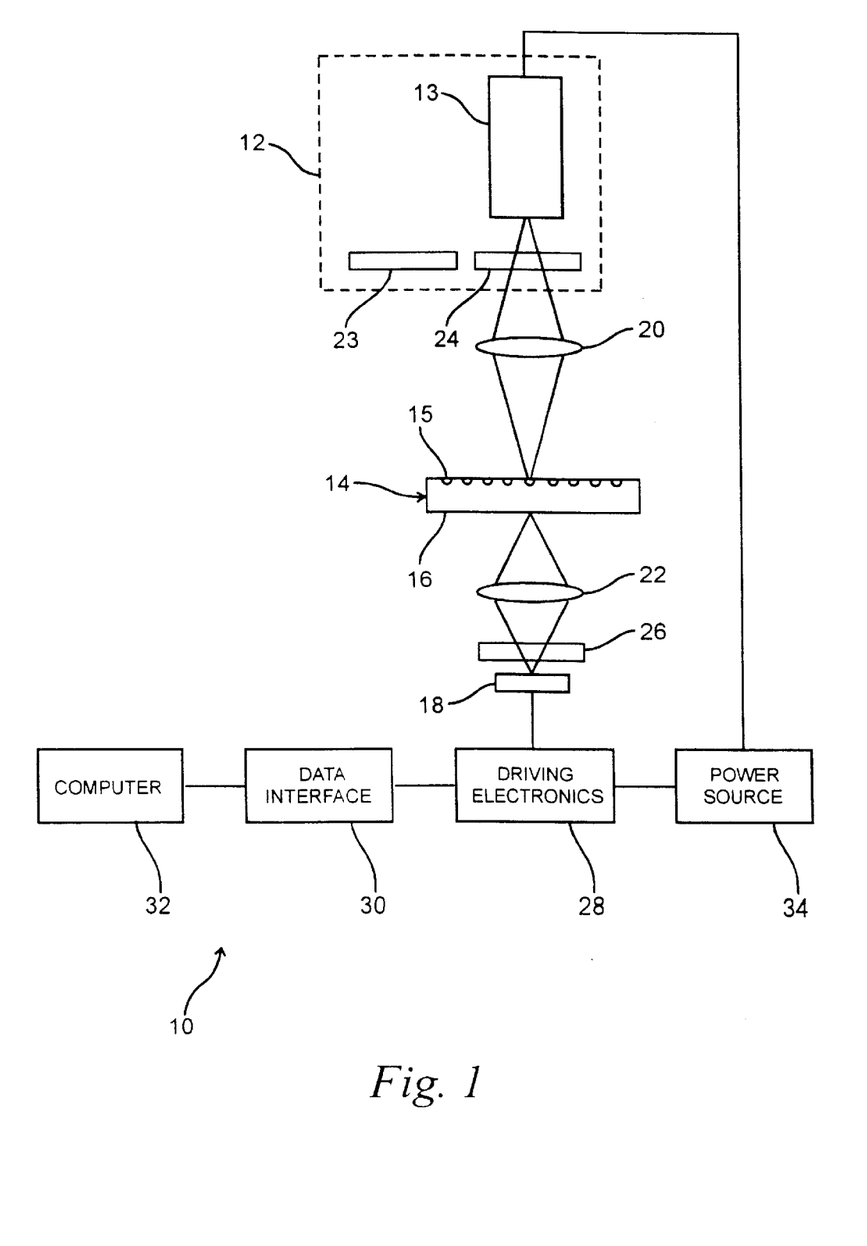
FIG. 1 is a diagram of a molecule detection system, in accordance with a preferred embodiment of the present invention.

Shown in FIG. 1 is a molecule detection system 10 for testing a sample for the presence of target molecules, in accordance with a preferred embodiment of the present invention. A source system 12, having a photon source 13, provides electromagnetic radiation directed to a molecular probe array 14. Array 14 typically comprises a plurality of test sites 15 formed into a substrate 16. Test sites 15 contain probe molecules that can bind to target molecules suspected of being present in the sample. An active pixel sensor 18 detects electromagnetic radiation from array 14. The electromagnetic radiation emitted from source system 12 and array 14 is preferably in the infrared, visible, or ultra-violet. Preferably, a source optical system 20 focuses the electromagnetic radiation from source system 12 onto array 14, and a detector optical system 22 focuses electromagnetic radiation emitted from array 14 onto active pixel sensor 18. Source system 12 may be provided with source filters 23 and 24 to filter the electromagnetic radiation from source 13, and a detector filter 26 may be provided to filter the electromagnetic radiation emitted from array 14. Driving electronics 28 are provided to control active pixel sensor 18. Preferably a data interface 30 is also provided to allow control of system 10 by a computer 32 and to allow for data transfer to and from computer 32. Alternatively, driving electronics 28 may be provided with a microprocessor (not shown) to control system 10, thereby obviating the need for computer 32. A power source 34 provides the electrical power needed to operate source 13, active pixel sensor 18, driving electronics 28, and data interface 30. Power source 34 is preferably a battery and may be as simple as a single 9-volt battery. System 10 is preferably provided as a portable system, and this is made possible by the use of active pixel sensor 18.

Preferably, source 13 produces electromagnetic radiation in only a narrow range of wavelengths and is easily portable. For example, source 13 could be a laser, such as a diode laser, or source 13 could be a light-emitting diode or an organic electro-luminescent device. Such sources typically produce electromagnetic radiation in only a single narrow wavelength range. However, source system 12 may also be configured to provide electromagnetic radiation in a plurality of wavelength ranges, preferably narrow wavelength ranges. For example, source 13 can be a broadband source, such as an arc lamp, in which case filters 23 and 24 may be used to select the desired range of wavelengths to be directed to array 14. Although source system 12 is shown in FIG. 1 with only two filters 23 and 24 for purposes of illustration, source system 12 may include a greater or fewer number of filters.

Figure 2:
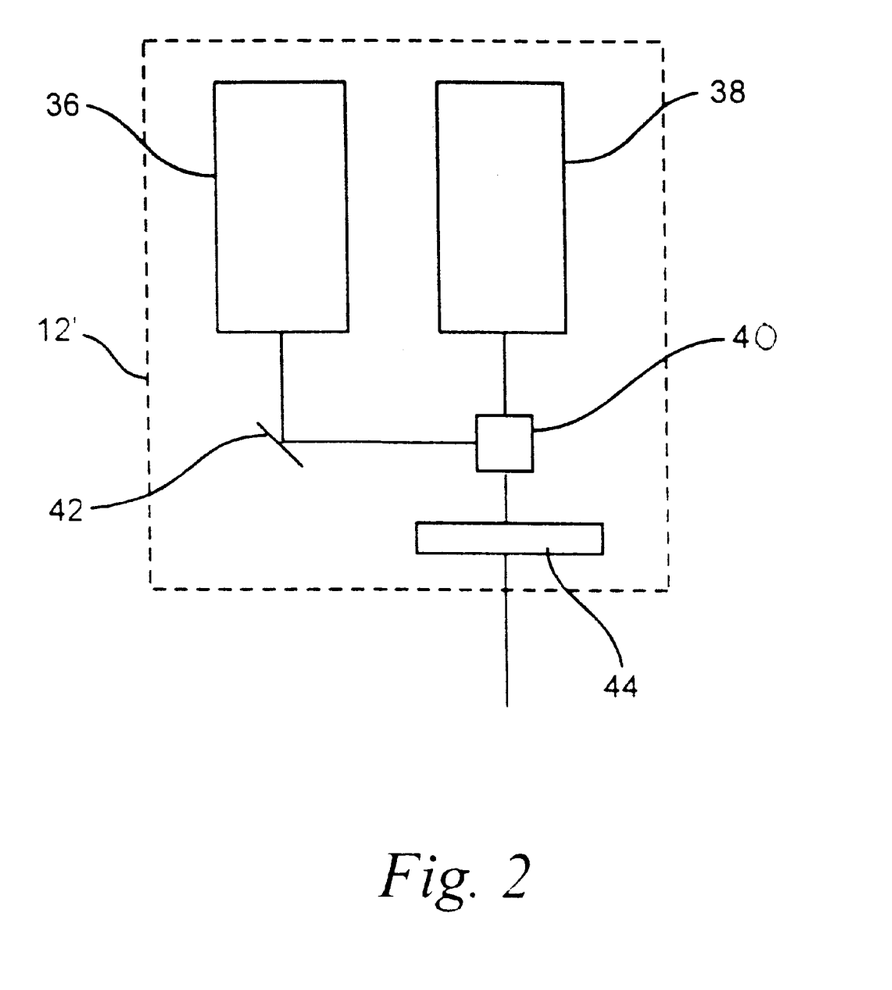
FIG. 2 is a diagram of an alternate source system for use in the molecule detection system of FIG. 1, in accordance with a preferred embodiment of the present invention.

An alternate source system 12' capable of providing electromagnetic radiation in a plurality of wavelength ranges is shown in FIG. 2. Source system 12' includes photon sources 36 and 38 that are preferably lasers. Sources 36 and 38 may be chosen such that they produce electromagnetic radiation in different wavelength ranges, so that by selecting the output from either source 36 or source 38, source system 12' is able to provide radiation in two different wavelength ranges. Additionally, although only two sources 36 and 38 are shown in FIG. 2, source system 12' may include a greater number. In general, source system 12' may be provided with a separate source for each wavelength range.

A more compact arrangement, however, may be provided by the use of non-linear optical elements. For example, as shown in FIG. 2, the output of source 38 is directed to a non-linear optical element 40, and the output of source 36 is directed to non-linear optical element 40 via a mirror 42. Non-linear optical element 40 combines the wavelengths from sources 36 and 38 to produce electromagnetic radiation having a shorter wavelength. A filter 44 may then be used to selectively pass this shorter wavelength radiation. Although a single non-linear optical element 40 is shown in FIG. 2 for purposes of illustration, a greater number maybe included in source system 12'. Additionally, the non-linear optical elements in source system 12' may combine wavelengths from more than one source, or they may change the wavelength from a single source. Thus, by using a plurality of sources and one or more non-linear optical elements, source system 12' can be configured to provide electromagnetic radiation in a plurality of desired wavelength ranges.

Figure 3:
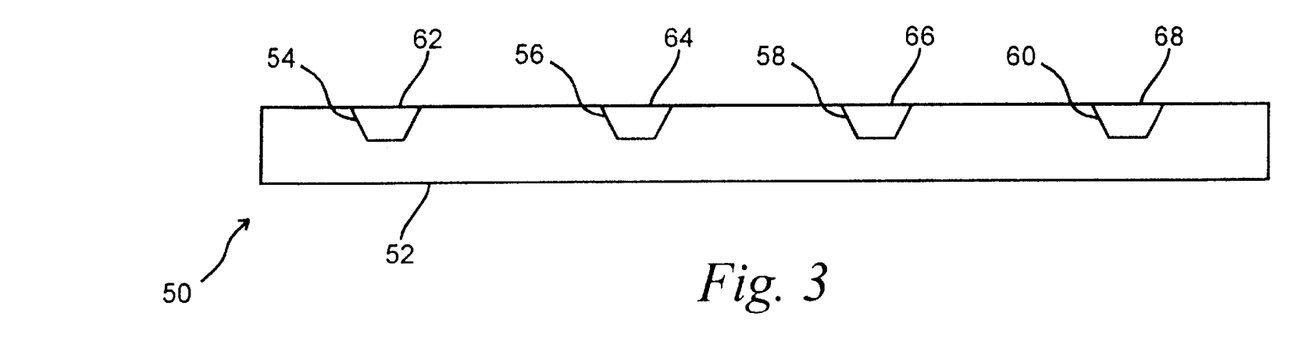
FIG. 3 is a cross-sectional view of an array of test sites, in accordance with a first preferred embodiment of the present invention.
Figure 4:
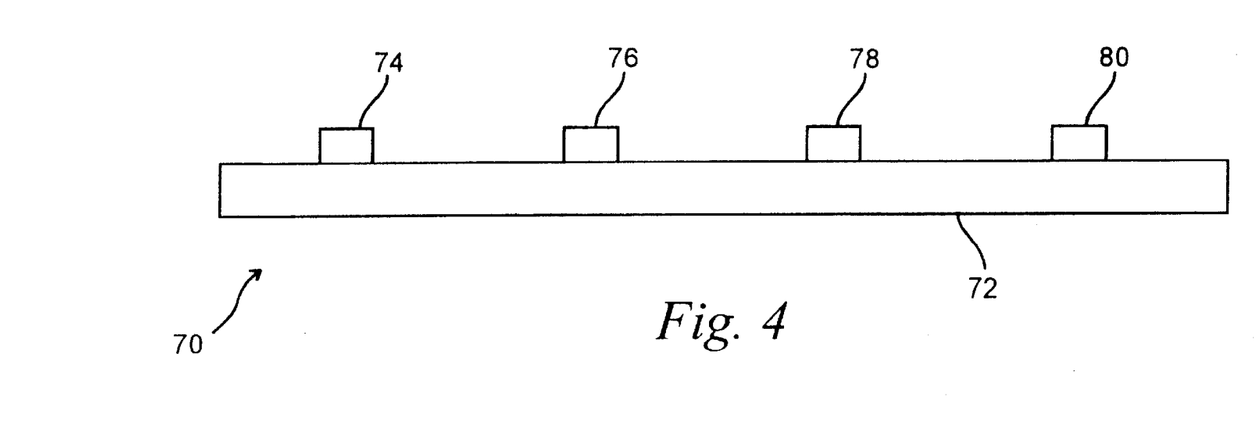
FIG. 4 is a cross-sectional view of an array of test sites, in accordance with a second preferred embodiment of the present invention.
Figure 5:
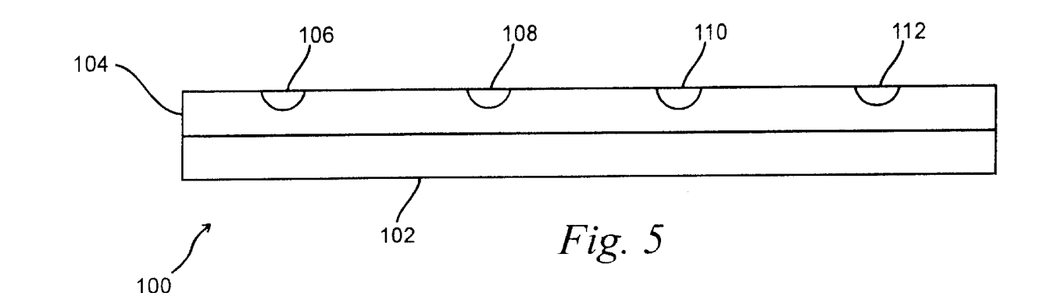
FIG. 5 is a cross-sectional view of an array of test sites, in accordance with a third preferred embodiment of the present invention.

Shown in FIGS. 3, 4, and 5 are three specific embodiments for array 14. With reference to FIG. 3, a first array embodiment 50 comprises a plurality of wells formed into a glass slide 52. For purposes of illustration, array 50 is shown in FIG. 3 with only four wells, namely wells 54–60, though array 50 can include a greater or fewer number of wells. Wells 54–60 may be formed into glass slide by conventional etching techniques. Disposed in wells 54–60 are corresponding gel portions 62–68. The gel is preferably a polyacrylamide gel. Probe molecules are disposed in gel portions 62–68, as described below in more detail. Alternatively, the probe molecules may be attached to the surfaces of wells 54–60, such as by using epoxysilane chemistry, instead of being suspended in gel.

With reference to FIG. 4, a second array embodiment 70 comprises a substantially flat substrate 72, such as a glass slide, on which are disposed islands of gel 74–80. The gel is preferably a polyacrylamide gel. Probe molecules are disposed gel islands 74–80, as described below in more detail. For purposes of illustration, array 70 is shown in FIG. 4 with only four gel islands 74–80, though array 70 can include a greater or fewer number of gel islands.

With reference to FIG. 5, a third array embodiment 100 comprises a glass slide 102 coated with a gel layer 104. Gel layer 104 preferably comprises a polyacrylamide gel. Gel layer 104 is provided with a plurality of test sites. For purposes of illustration, array 100 is shown in FIG. 5 with only four test sites, namely sites 106–112, though a greater or fewer number of test sites may also be provided. Each test site 106–112 is defined by the region where added probe molecules have diffused into gel layer 104. Probe molecules may be added to gel layer 104 by any means suitable for adding small amounts of material, such as micropipetting.

Figure 6:
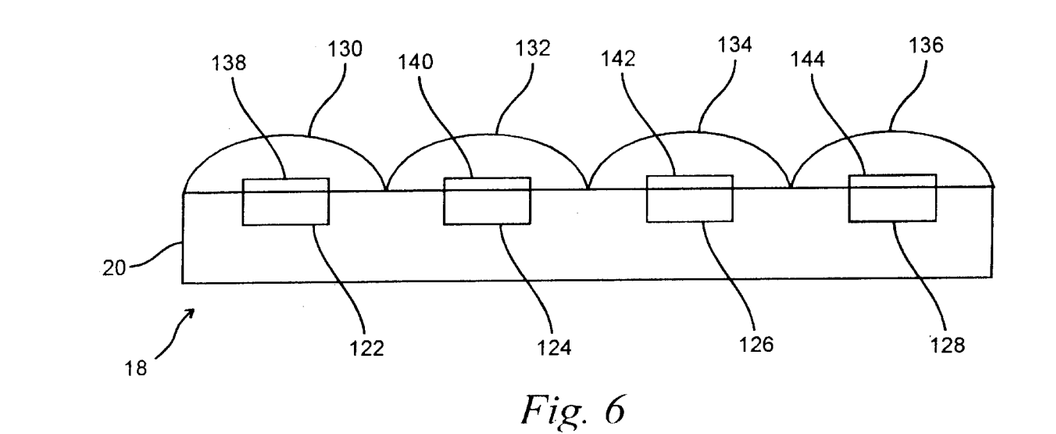
FIG. 6 is a cross-sectional view of an active pixel sensor, in accordance with a preferred embodiment of the present invention.

With reference to FIG. 6, there is shown a representative active pixel sensor 18. Active pixel sensor 18 comprises a plurality of pixel cells formed into a substrate 120. For purposes of illustration, active pixel sensor 18 is shown in FIG. 5 with only four pixel cells 122–128, though active pixel sensor 18 will typically have a far greater number. Each of pixel cells 122–128 typically includes a photogate (not shown), a charge transfer section (not shown), and a readout circuit (not shown). An example of a suitable active pixel sensor is the SCM20014, sold by Motorola, Inc. The data sheets for the SCM20014 (Aug. 9, 1999 version) are fully incorporated herein by reference. The SCM20014 is beneficially provided with correlated double sampling and frame rate clamping to reduce fixed pattern noise. The SCM20014 is also provided with electronic shuttering, whereby the exposure time of the pixels can be controlled electronically. This eliminates the need for an external shutter, thereby further simplifying system 10. Preferably, SCM20014 is run in digital mode in order to take advantage of its digital signal processing capabilities, such as data companding.

With reference to FIG. 1, detector optical system 22 preferably focuses each test site in array 14 onto one or more pixel cells of active pixel sensor 18. For example, with reference to FIGS. 5 and 6, each of test sites 106–112 may be focused onto a corresponding one of pixel cells 122–128. In order to improve their light-gathering ability, pixel cells 122–128 are preferably provided with microlenses 130–136, respectively. The best sensitivity is typically achieved by imaging each test site onto only a single pixel of active pixel sensor 18. However, to provide higher spatial resolution, such as to resolve different regions within a given test site, each test site may instead be focused onto a plurality of pixels of active pixel sensor 18.

Alternatively, instead of using detector optical system 22, substrate 16 of array 14 may be attached directly to active pixel sensor 18. For example, active pixel sensor 18 may be fabricated with a $SiO_2$ layer on top of the pixels. Either a layer of gel or islands of gel may then be placed on top of this $SiO_2$ layer. Alternatively, substrate 16 of array 14 may be built out of glass on top of this $SiO_2$ layer.

Each of pixel cells 122–128 is also preferably provided with a color filter 138–144, respectively. Each of color filters 138–144 is designed to allow only a certain desired range of wavelengths to pass to pixel cell 122–128 for detection, as described in more detail below. Each of color filters 138–144 can comprise a layer of polyimide resin that has been dyed to provide the desired wavelength response. Color filters 138–144 can each have the same or different wavelength responses.

System 10 may be used to detect one or more types of target molecules in a sample in the following way. Probe molecules of known type are added to test sites 15 in array 14, such as by micropipetting. The probe molecules are chosen so as to be able to bind with the target molecules that are suspected of being present in the sample to form bound complexes. Accordingly, what probe molecules are used will depend on what target molecules are to be detected. To detect antigens in the sample, the probe molecules are preferably the corresponding antibody. To detect antibodies in the sample, the probe molecules are preferably the corresponding antigen. To detect nucleic acids in the sample, the probe molecules should have nucleotide sequences that are complementary to at least a portion of the nucleotide sequence that the nucleic acids may have. Other types of target molecules may also be detected by using appropriate probe molecules that are able to bind with them.

The probe molecules added to test sites 15 may all be of the same type. Alternatively, different types of probe molecules may be added to different test sites. In this way, different certain test sites can be made sensitive to different types of target molecules and can be used to characterize the nature of the target molecules present in the sample.

For example, with reference to array 100 in FIG. 5, the probe molecules present in test sites 106–112 may be oligonucleotides, each having a different nucleotide sequence. Thus, if binding were to occur in only site 110, then it could be determined that the nucleic acids in the sample had the nucleotide sequence complementary to site 110 but lacked the nucleotide sequence complementary to sites 106, 108, and 112. Similarly, if binding were to occur in all of sites 106–112, and the sample included only one type of nucleic acid, then one could infer that the target nucleic acid included nucleotide sequences complementary to the nucleotide sequences of all of sites 106–112.

After the probe molecules are disposed in test sites 15, the sample is then added to test sites 15. For example, portions of the sample may be micropipetted onto each of test sites 15. Alternatively, test sites 15 may be immersed in the sample. However, other means of exposure could also be used. After the sample is allowed to bind with the probe molecules in test sites 15, array 14 is preferably rinsed to remove unreacted sample.

To facilitate optical detection, the target molecules in the sample may be conjugated to a fluorophore before they are exposed to the probe molecules. Many molecules of biological interest, such as proteins and nucleic acids, can be conjugated to fluorophores using well-known techniques. Table 1 lists some examples of suitable fluorophores, but many others could also be used. If the target molecules are not conjugated to fluorophores, then optical detection may also facilitated by exposing the bound complexes in test sites 15 to a selective dye, such as ethidium bromide, as described above, or to fluorescent reporter molecules, as described in more detail below. Bound complexes in test sites 15 can also be made luminescent in other ways so as to facilitate optical detection. For example, the bound complexes in test sites 15 could also be phosphorescent, chemiluminescent, bioluminescent, electro-luminescent, or electro-chemiluminescent. Alternatively, the bound complexes may not be luminescent at all. Instead, binding may be detected by measuring the absorbance of the bound complexes at a given wavelength.

TABLE 1

| Fluorescent Dye Trade Name | Excitation Wavelength (in nanometers) | Fluorescence Wavelength (in nanometers) |
| --- | --- | --- |
| ALEXA FLUOR 350 | 346 | 442 |
| ALEXA FLUOR 430 | 431 | 541 |
| ALEXA FLUOR 532 | 531 | 554 |
| ALEXA FLUOR 568 | 578 | 603 |
| BODIPY 650 | 643 | 666 |

Once target molecules in the sample have had an opportunity to bind with probe molecules in test sites 15 to form bound complexes, array 14 is exposed to incident electromagnetic radiation from source system 12. The wavelength used for the incident radiation will depend on a number of factors. If the target molecules have been conjugated to a fluorophore, then the wavelength of the incident radiation is chosen to correspond to the excitation wavelength of the fluorophore. Table 1 lists the excitation wavelengths typically used for a number of different fluorophores. If a selective dye, such as ethidium bromide, is also intercalated into the bound complexes, then the wavelength of the incident radiation is preferably chosen to be the excitation wavelength of the selective dye. If the bound complexes are exposed to fluorescent reporter molecules, then the wavelength is chosen to be the excitation wavelength for the reporter molecules. If the bound complexes are phosphorescent, then the wavelength is chosen so as to induce the phosphorescence. If the bound complexes are not luminescent at all, then the wavelength of the incident radiation is preferably chosen so that the bound complexes will have a substantially different absorbance than unbound probe molecules.

Active pixel sensor 18 is then used to detect the electromagnetic radiation emitted from array 14. If the bound complexes are fluorescent or have been made fluorescent by exposure to selective dyes or fluorescent reporter molecules, then detection occurs during illumination from source system 12, and the emitted radiation of interest will be the fluorescence radiation emitted by that fluorophore. Table 1 lists the range of wavelengths characteristically emitted by a number of different fluorophores. The pixels of sensor 18 are preferably provided with filters, such as filters 138–144 described above, that block the wavelength of the incident radiation and pass the wavelengths characteristic for the fluorescence radiation, so that the pixels will detect primarily the fluorescence radiation, rather than the incident radiation. Alternatively, instead of fabricating filters into active pixel sensor 18, a separate detector filter 26 may be used. In order to further reduce the amount of incident radiation that may be detected by active pixel sensor 18, active pixel sensor 18 may be oriented at an angle such that neither the incident radiation passing through array 14 nor the incident radiation specularly reflected from array 14 fall on active pixel sensor 18. For example, source system 12 and active pixel sensor 18 may be located on the same side of array 14. Alternatively, a wavelength-dependent beam splitter (not shown) may be placed in the path of the incident radiation between source system 12 and array 14 that preferentially directs the fluorescence radiation toward active pixel sensor 18. Binding is then detected by the presence of fluorescence radiation, i.e., by detecting an increase in the detected light level, as compared to a control. The control could be, for example, the light level detected before binding.

If the absorbance of the bound complexes is to be measured, then filters to block the incident radiation are not necessary. Instead, the test sites with bound complexes are detected by an increase in absorbance of the incident radiation, i.e., a decrease in the detected light level as compared to a control. The control could be, for example, the light level detected before binding.

If the bound complexes are phosphorescent, then active pixel sensor 18 detects the electromagnetic radiation emitted from test sites 15 only after the illumination from source system 12 ceases. Accordingly, active pixel sensor 18 is preferably provided with an electronic shuttering capability. Specifically, source system 12 illuminates test sites 15 while active pixel sensor 18 is electronically shuttered to allow bound complexes to absorb the incident radiation. Then, source system 12 is turned off or blocked, and active pixel 18 is enabled to detect phosphorescence from the bound complexes in test sites 15. Notably, because the incident radiation is not present during detection filters between active pixel sensor 18 and array 14 are not necessary.

If the bound complexes are chemiluminescent, bioluminescent, electro-luminescent, or electro-chemiluminescent, then source system 12 is not needed. Instead, the luminescence from the bound complexes in test sites 15 is simply detected by active pixel sensor 18.

An important advantage of having the probe molecules disposed in a gel, such as in array 50, 70, or 100, is that fluorescence radiation emitted from the bound complexes in the test sites can be made more spatially concentrated. In particular, the bound complexes will be arranged in a three-dimensional pattern in the gel. In contrast, if the same number of probe molecules are arranged in a two-dimensional pattern, such as being attached to the surfaces of wells 54–60, then the resulting bound complexes will be more spread out, and the intensity of the resulting signal will be reduced. Accordingly, the binding of probe molecules is more easily detected when the probe molecules are disposed in a gel rather than when they are attached to a surface.

An embodiment of system 10 can also be used for "multi-color" tests. In multi-color tests, multiple fluorophores are used, with each fluorophore emitting fluorescence radiation in a distinct range of wavelengths. Multiple filters are used so that active pixel sensor 18 detects the fluorescence radiation from only one fluorophore at a time. The multiple filters are preferably integral to active pixel sensor 18, such as filters 138–144 shown in FIG. 6. Alternatively, filter 26 can be changed to detect each fluorophore.

Figure 7A:
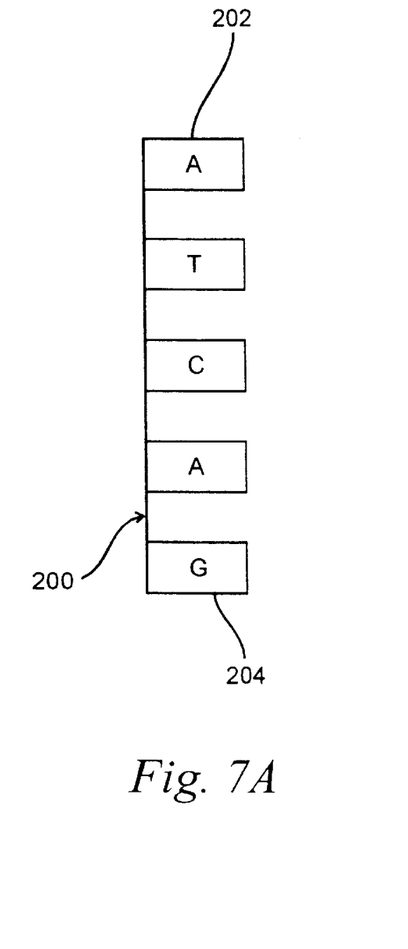
FIG. 7A illustrates a first step in a 3' offset single-base extension test, in accordance with a preferred embodiment of the present invention.
Figure 7B:
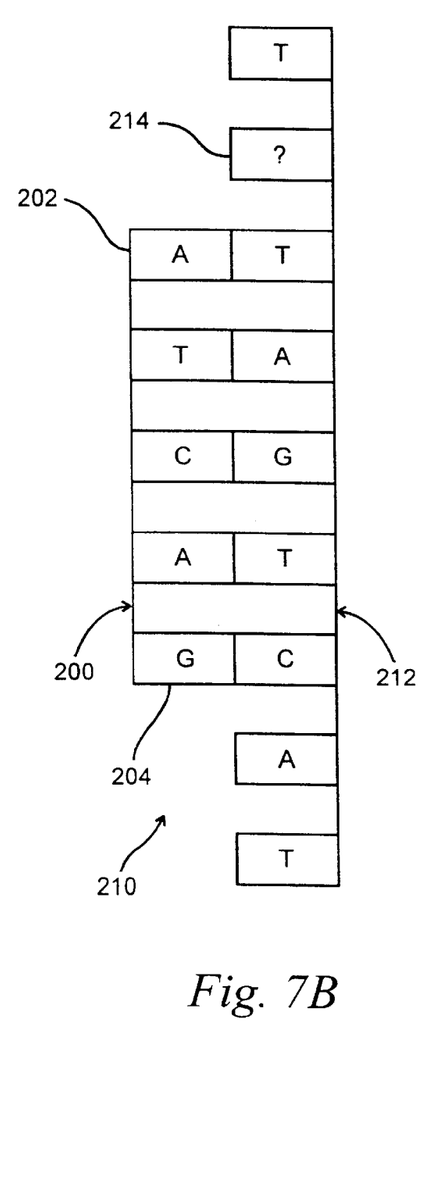
FIG. 7B illustrates a second step in a 3' offset single-base extension test, in accordance with a preferred embodiment of the present invention.
Figure 7C:
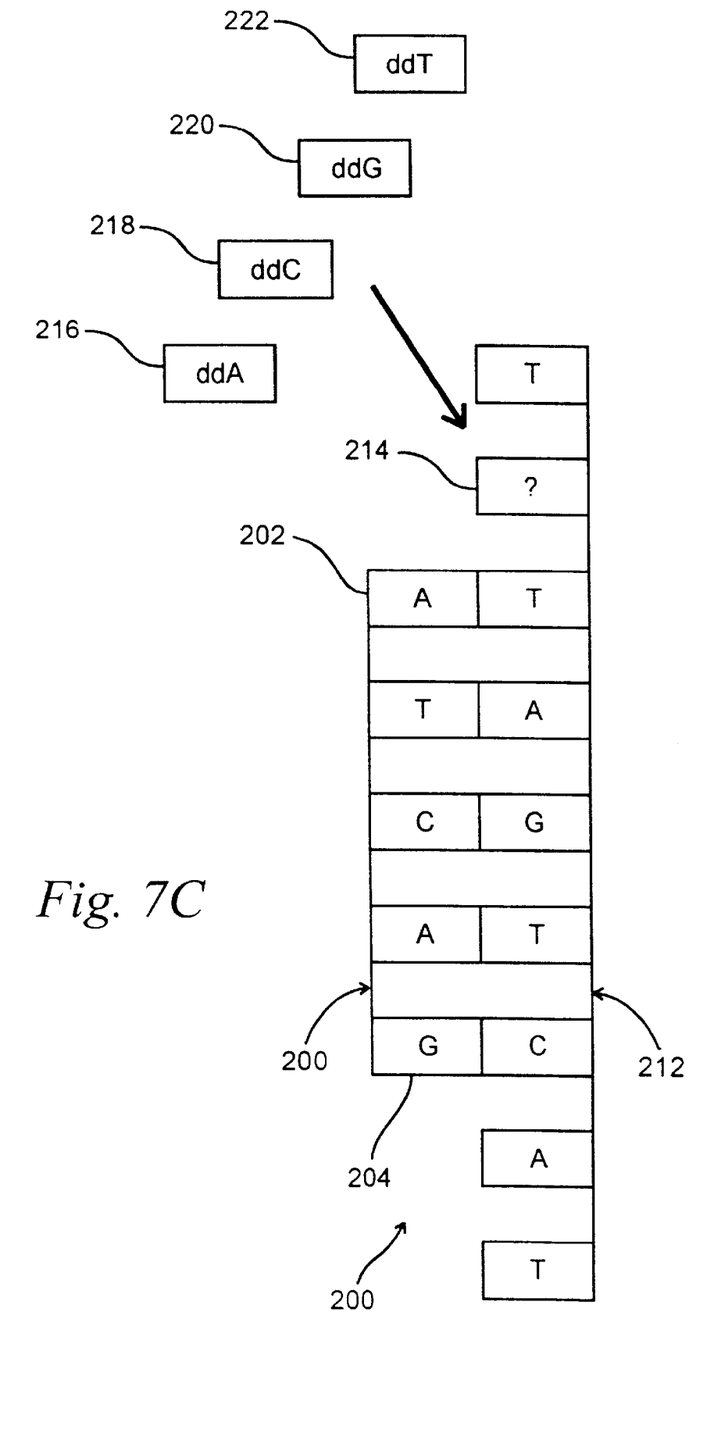
FIG. 7C illustrates a third step in a 3' offset single-base extension test, in accordance with a preferred embodiment of the present invention.

Single-base extension tests comprise an important class of multi-color test. Single-base extension tests may be used to identify unknown nucleotides in nucleic acids present in a sample. An example of a 3' offset single-base extension test is illustrated in FIGS. 7A–C. Shown in FIG. 7A is a probe molecule 200 comprising a sequence of five nucleotides and having a 3' end 202 and a 5' end 204. Probe molecule 200 is disposed in a given test site, such as site 106 in FIG. 5. Shown in FIG. 7B is a bound complex 210 formed after a sample containing a target nucleic acid 212 has been added to site 106. In this case, hybridization occurs because probe molecule 200 contains a nucleotide sequence that is complementary to a nucleotide sequence present in target nucleic acid 212. As shown in FIG. 7B, target nucleic acid 212 has an unknown nucleotide 214 adjacent the nucleotide of nucleic acid 212 that hybridized with the nucleotide at 3' prime end 202 of probe molecule 200. If any unbound sample remains in test site 106 after binding is completed, it may be removed in a rinse step.

The goal of the single-base extension test is to identify unknown nucleotide 214. To make the identification, bound complex 210 in site 106 is exposed to reporter molecules 216–222, as shown in FIG. 7C. Each of reporter molecules 216–222 comprises a single nucleotide base conjugated to a distinct fluorophore. For example, reporter 216 may comprise adenine conjugated to ALEXA FLUOR 350; reporter 218 may comprise cytosine conjugated to ALEXA FLUOR 532; reporter 210 may comprise guanine conjugated to ALEXA FLUOR 568; and reporter 212 may comprise thymine conjugated to BODIPY 650. The identity of unknown nucleotide 214 will determine which of reporters 216–222 will bind to it.

After allowing sufficient time for such binding, any remaining reporter molecules 216–222 are removed by rinsing site 106. Site 106 in array 14 is then exposed to radiation from source system 12 at the various wavelengths required to cause fluorescence in reporters 216–222 in succession. Thus, in the example described above, array 14 would be exposed successively to incident radiation at wavelengths 346 nm (for reporter 216), 531 nm (for reporter 218), 578 nm (for reporter 220), and 643 nm (for reporter 222).

To perform the 3' offset single-base extension test, test site 106 is imaged, such as by using optical system 22, onto at least four pixels of active pixel sensor 18, such as pixels 122–128 shown in FIG. 6. To conduct multi-color tests, each of filters 138–144 on pixels 122–128, respectively, is designed to pass the fluorescence radiation of one of the four fluorophores while blocking the excitation wavelength used for that fluorophore. As a result, pixels 122–128 serve to detect fluorescence radiation from reporters 216–222, respectively. The identity of unknown nucleotide 214 can then be determined based on whichever of pixels 122–128 detects a substantial increase in fluorescence radiation, as compared to a control. The control may, for example, be the amount of radiation detected by the pixel before reporter molecules 216–222 were added. As a specific example, if only pixel 128 detected a substantial increase, then one could infer that reporter 220, comprising guanine, had hybridized with nucleotide 214, so that nucleotide 214 must be cytosine.

Figure 8:
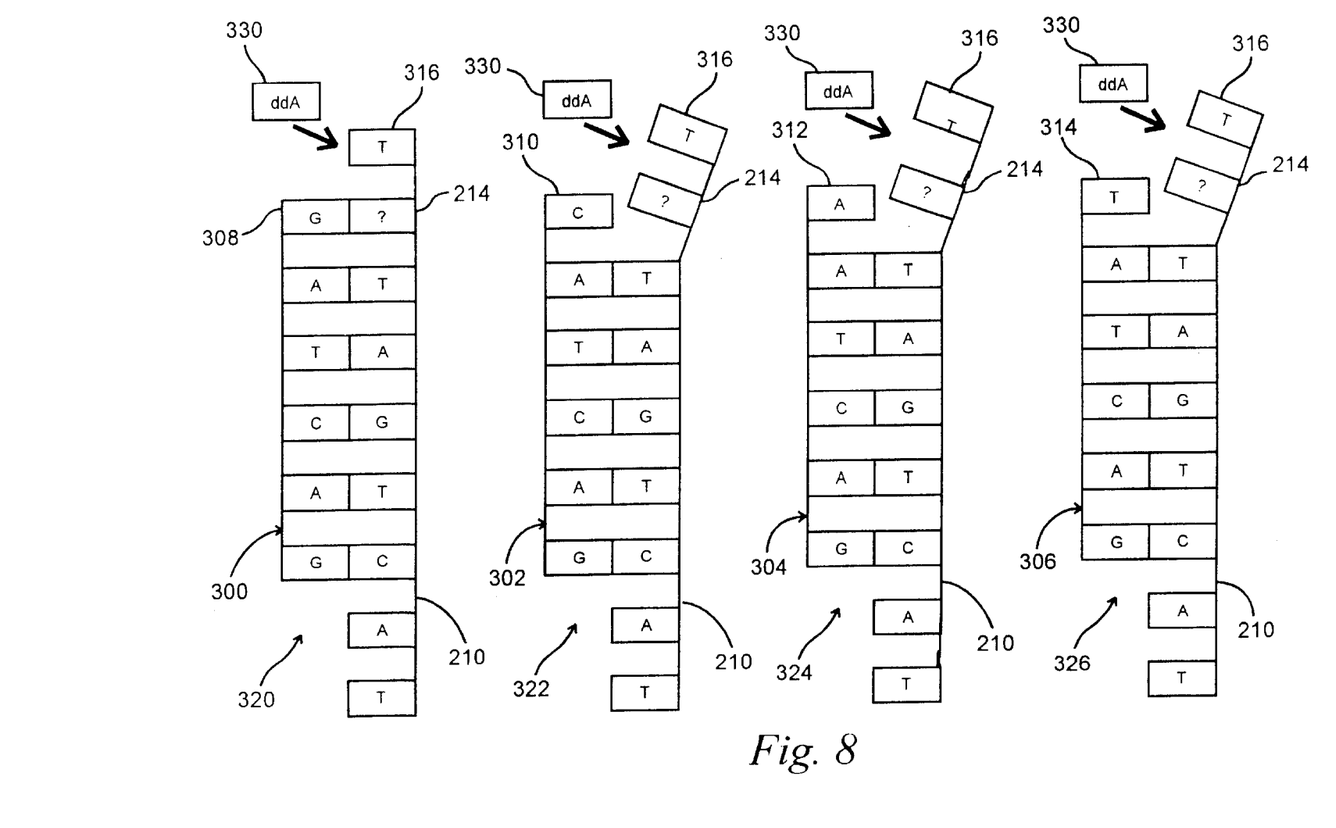
FIG. 8 illustrates a 3' inclusive single-base extension test, in accordance with a preferred embodiment of the present invention.

The 3' inclusive single-base extension test, illustrated in FIG. 8, is an alternative way to identify an unknown nucleotide in a nucleic acid. Four different probe molecules 300–306 are disposed in four different test sites, such as test sites 106–112 in FIG. 5. Probe molecules 300–306 are distinguished from each other by the nucleotide present at the 3' end. In particular, at the 3' end, probe 300 has a guanine nucleotide, probe 302 has a cytosine nucleotide, probe 304 has an adenine nucleotide, and probe 306 has a thymine nucleotide. Probe molecules 300–306 disposed in test sites 106–112 are then exposed to a sample containing nucleic acid 210. Nucleic acid 210 has an unknown nucleotide 214 (which is actually cytosine), and a known nucleotide 316 (e.g., thymine) adjacent to unknown nucleotide 214. Nucleic acid 210 is able to hybridize with each of probes 300–306, to form bound complexes 320–326, respectively. However, because unknown nucleotide 214 is actually cytosine, nucleotide 214 is hybridized with the nucleotide at the 3' end of the probe molecule only in bound complex 320. This hybridization of unknown nucleotide 214 may then be detected by exposing bound complexes 320–326 to a reporter 330, comprising an adenine nucleotide conjugated to a fluorophore, as reporter 330 will hybridize only with bound complex 320. After reporter molecules 330 are given sufficient time to bind to bound complexes 320–326, any excess may be rinsed away. Array 14 is exposed to electromagnetic radiation from source at the fluorophore's excitation wavelength. Test sites 106–112 are imaged onto pixels 122–128, respectively, and either integral filters 138–144 or detector filter 26 are provided to block the excitation wavelength and pass the fluorescence radiation. In this way, the identity of unknown nucleotide 214 may be determined based on which of pixels 122–128 detect fluorescence radiation.

Active pixel sensor 18 in system 10 can be also used for time-resolved studies. In such time-resolved studies, one or more pixels of active pixel sensor 18 measure the electromagnetic radiation from one or more of test sites 15 of array 14 at successive time intervals. By comparing the measurements from successive time intervals the population of specified molecules in test sites 15 can be monitored as a function of time. For example, the binding of probe molecules with target molecules to form bound complexes in test sites 15 can be monitored as a function of time by active pixel sensor 18 monitoring the optical properties of test sites 15. In this way, it can be determined when the binding process is complete. The optical properties measured by active pixel sensor 18 can be the absorbance of test sites 15 of incident electromagnetic radiation of a given wavelength from source system 12, as described above. Alternatively, the bound complexes in test sites 15 may be luminescent, either fluorescent, phosphorescent, chemiluminescent, bioluminescent, electro-luminescent, or electro-chemiluminescent, in which case active pixel sensor 18 can monitor the population of bound complexes by detecting the luminescence from the bound complexes, as described above. To do time resolved studies, active pixel sensor 18 would simply take measurements at successive time intervals.

Figure 9:
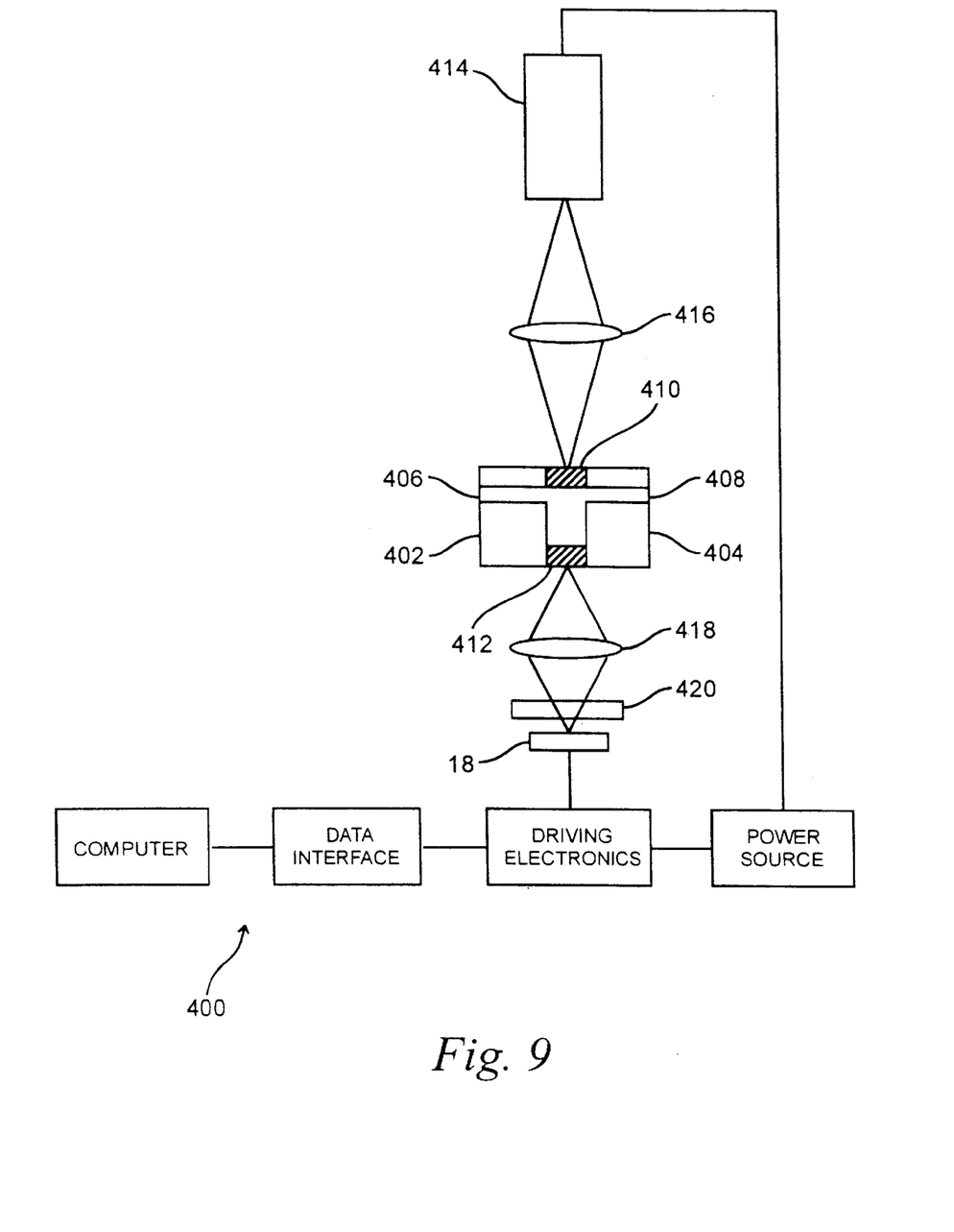
FIG. 9 is a diagram of a molecule detection system, with an amplification device shown in cross-section, in accordance with a preferred embodiment of the present invention.

Another important time-resolved application for active pixel sensor 18 is the monitoring of the population of nucleic acids amplified by processes such as the polymerase chain reaction (PCR). For example, shown in FIG. 9 is a molecule detection system 400 that includes an amplification device 402. A nucleic acid amplification process, such as PCR, is conducted in an amplification chamber 404 formed in amplification device 402. Amplification device 402 is also provided with an input port 406, connected to amplification chamber 404, for adding the chemicals needed to perform PCR, and amplification device 402 is provided with an output port 408, connected to amplification chamber 404, for removal of the products. To allow optical detection of the amplified nucleic acids in amplification chamber 404, amplification device 402 may be provided with optically transparent windows 410 and 412 at the top and bottom, respectively, of amplification chamber 402. Alternatively, amplification device 402 may itself be made out of an optically transparent material, such as glass.

Active pixel sensor 18 may monitor the population of amplified nucleic acids either by measuring the absorbance of incident electromagnetic radiation at a given wavelength passing through amplification chamber 404 or by measuring the fluorescence from the amplified nucleic acids in amplification chamber 404. In either approach, a source system 414, which may be configured similarly to source systems 12 and 12' described above, provides incident electromagnetic radiation directed to amplification chamber 404, and active pixel sensor 18 detects the electromagnetic radiation from amplification chamber 404 through bottom window 412. A source optical system 416 may be used to focus the incident electromagnetic radiation from source system 414 into amplification chamber 404, and a detector optical system 418 may be used to image selected areas in amplification chamber 404 onto active pixel sensor 18. To monitor the fluorescence of the amplified nucleic acids in amplification chamber 404, a detector filter 420 preferably interposes amplification chamber 404 and active pixel sensor 18 to filter out the wavelengths corresponding to the incident radiation and pass the wavelengths corresponding to the fluorescence radiation. Detector filter 420 may be integral to active pixel sensor 18, as described above. In system 400, active pixel sensor 18 can take measurements at successive time intervals to monitor the progress of the amplification process.

Figure 10:
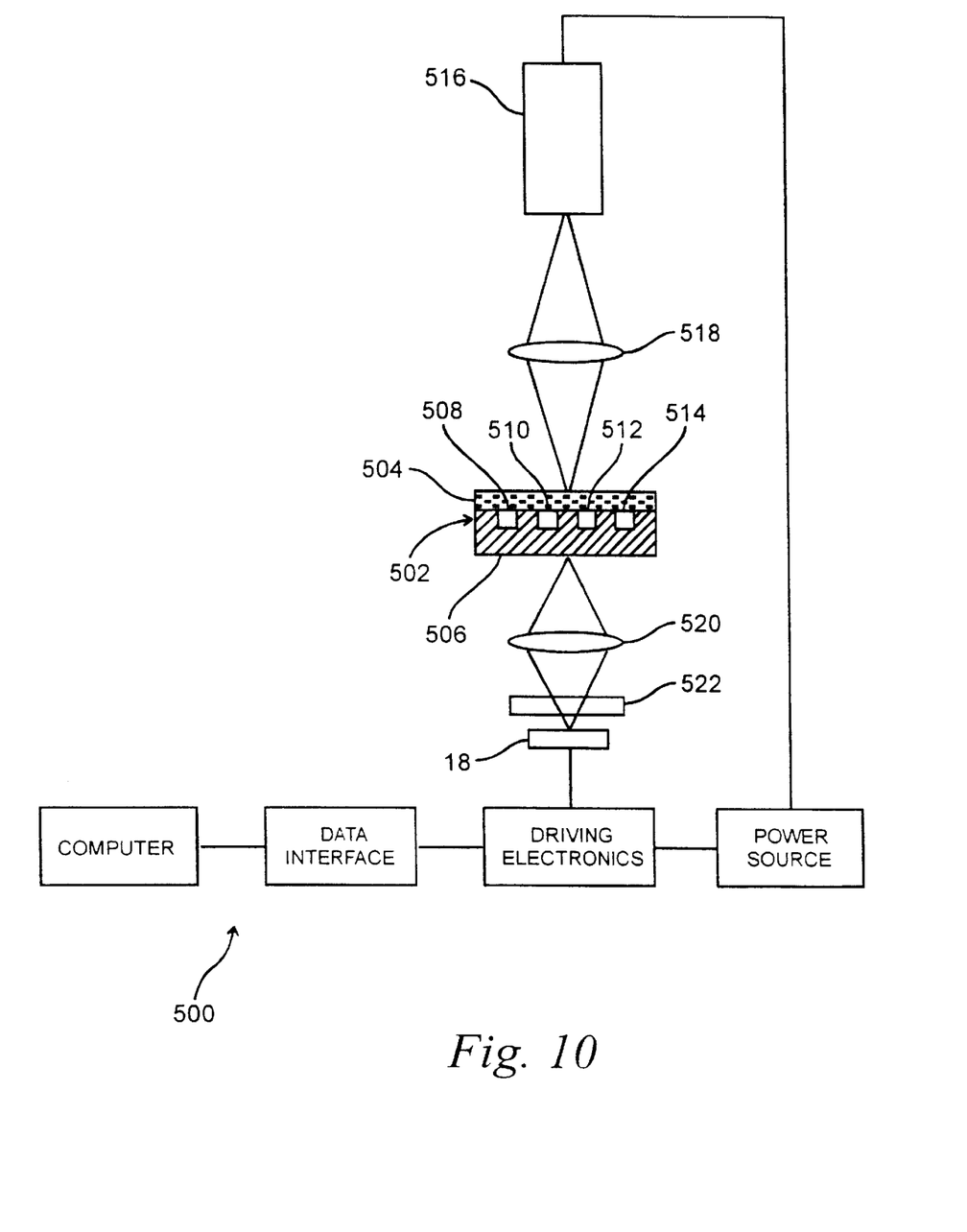
FIG. 10 is a diagram of a molecule detection system, with a capillary electrophoresis device shown in cross-section, in accordance with a preferred embodiment of the present invention.

As another time-resolved application, active pixel sensor 18 may be used to detect the presence of specified molecules separated by processes such as capillary electrophoresis. For example, shown in FIG. 10 is a molecule detection system 500 that includes a capillary electrophoresis device 502. Capillary electrophoresis device 502 is preferably a microfluidic device comprising a top layer 504 attached to a substrate layer 506. Capillary electrophoresis channels 508–514 are formed into substrate layer 506. Though only four electrophoresis channels are shown for purposes of illustration, electrophoresis device 502 may include a greater or lesser number. Preferably, layers 504 and 506 are made out of an optically transparent material, such as glass or fused silica, to allow optical detection of the components separated in electrophoresis channels 508–514. Alternatively, electrophoresis device 502 may be provided with optically transparent windows (not shown). The specified molecules may be luminescent, most typically fluorescent, in which case they may be detected by their luminescence. Alternatively, the specified molecules may be detected by their absorbance. A source system 516 provides incident electromagnetic radiation directed to electrophoresis device 502. A source optical system 518 preferably focuses the incident radiation into each of electrophoresis channels 508–514. For example, source optical system 516 may include a cylindrical lens that focuses the incident radiation into a line cutting transversely across channels 508–514. Active pixel sensor 18 detects the electromagnetic radiation from specified locations in each of channels 508–514. A detector optical system 520 may be used to image the specified locations in channels 508–514 onto active pixel sensor 18. Preferably, different channels are imaged onto different pixels of active pixel sensor 18. For example, channels 508–514 may be imaged onto pixels 122–128, respectively. In this way, channels 508–514 may be monitored simultaneously. For detecting fluorescence radiation, a detector filter 522 may be provided, and detector filter 522 may be integral to active pixel sensor 18. Active pixel sensor 18 takes measurements at successive time intervals during the electrophoretic separation process when the various chemical components added to device 502 migrate along channels 508–514 and become separated. In this way, system 500 can be used to determine when specified molecules pass the specified locations along channels 508–514 monitored by active pixel sensor 18.

Figure 11:
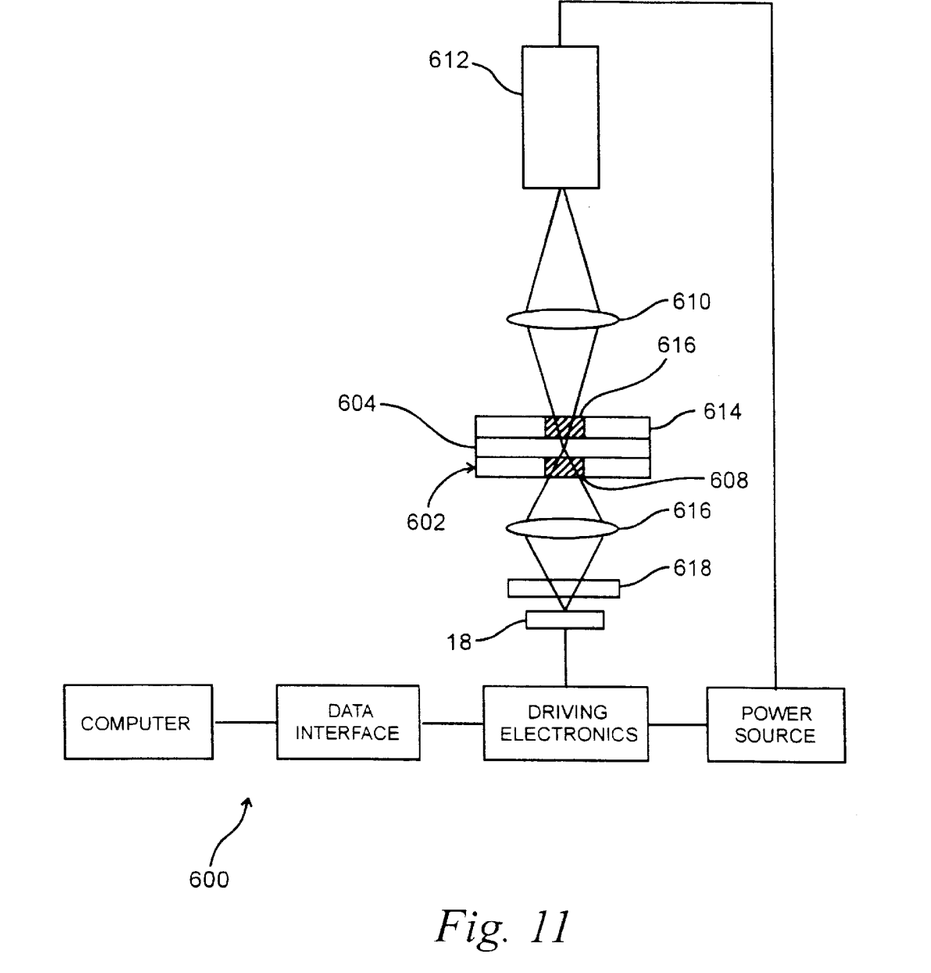
FIG. 11 is a diagram of a molecule detection system, with a flow cell shown in cross-section, in accordance with a preferred embodiment of the present invention.

In a similar time-resolved application, active pixel sensor 18 may be used to determine when specified molecules pass a given location in a flow cell. The specified molecules may be luminescent, such as fluorescent, or they my be detected by their absorbance at a given wavelength. Shown in FIG. 11 is a molecule detection system 600 including a flow cell 602. Flow cell 602 includes a channel 604 and optically transparent windows 606 and 608. Alternatively, flow cell 602 may be made out of an optically transparent material. An optical system 610 focuses incident electromagnetic radiation from source system 612 to a given location 614 within channel 604. A detector optical system 616 images electromagnetic radiation from point 614 onto active pixel sensor 18. A detector filter 618 may also be provided, as shown in FIG. 11. By monitoring how the electromagnetic radiation detected by active pixel sensor 18 changes as a function of time, system 600 can be used to detect when the specified molecules pass point 614 in flow cell 602. For example, if the specified molecules are fluorescent, the arrival of the specified molecules at location 614 would be detected by active pixel sensor 18 as an increase in the measured amount of fluorescence radiation. If the specified molecules are to be detected by their absorbance of the incident radiation, then the arrival of the specified molecules at location 614 would be detected by active pixel sensor 18 as a decrease in detected radiation.

Additionally, a device, such as a microfluidic device, may have more than one component monitored by an active pixel sensor. For example, a microfluidic device may include a PCR chamber in one section and a capillary electrophoresis channel in another section, with each section being monitored by a separate active pixel sensor. Accordingly, the molecule detection systems of the present invention may, in general, include more than one active pixel sensor.

Although various embodiments of this invention have been shown and described, it is to be understood that various modifications and substitutions, as well as rearrangements and combinations of the preceding embodiments, can be made by those skilled in the art, without departing from the novel spirit and scope of this invention.

What is claimed is:

1. A method for testing a sample for the presence of target molecules, said method comprising the steps of:
   a) providing a test site, said test site comprising probe molecules;
   b) contacting said sample comprising target molecules with said test site to form bound complexes;
   c) illuminating said test site with incident electromagnetic radiation, said incident electromagnetic radiation including radiation at a first wavelength; and
   d) detecting electromagnetic radiation from said test site with at least one pixel of an active pixel sensor.

2. The method of claim 1 further comprising the step of comparing the amount of electromagnetic radiation detected by said at least one pixel with a control.

3. The method of claim 2, wherein the absorbance at said first wavelength of said bound complexes is substantially different than the absorbance at said first wavelength of said probe molecules.

4. The method of claim 3, wherein said bound complexes are fluorescent, said bound complexes absorbing said incident electromagnetic radiation at said first wavelength and emitting fluorescence radiation at a second wavelength, said method further comprising filtering said electromagnetic radiation reaching said at least one pixel from said test site so as to block said first wavelength and to pass said second wavelength.

5. The method of claim 3, wherein said bound complexes are phosphorescent, said bound complexes emitting phosphorescence radiation at a second wavelength after absorbing said incident radiation at said first wavelength, said method further comprising shuttering said active pixel sensor, blocking electromagnetic radiation from at least one pixel while said test site is illuminated with incident electromagnetic radiation, and detecting electromagnetic radiation from said test site with said at least one pixel when said test site is not illuminated with said incident radiation.

6. In a system comprising an active pixel sensor, said active pixel sensor comprising at least a first pixel, a second pixel, a third pixel, and a fourth pixel, a method for identifying an unknown nucleotide in a nucleic acid, said nucleic acid having a nucleotide sequence adjacent said unknown nucleotide, said method comprising:

a) providing a test site, said test site comprising probe molecules;

b) contacting said sample comprising target molecules with said test site to form bound complexes;

c) adding first reporter molecules to said test site, said first reporter molecules comprising adenine conjugated to a first fluorophore, said first fluorophore emitting electromagnetic radiation at a first fluorescence wavelength when exposed to electromagnetic radiation at a first excitation wavelength;

d) adding second reporter molecules to said test site, said second reporter molecules comprising cytosine conjugated to a second fluorophore, said second fluorophore emitting electromagnetic radiation at a second fluorescence wavelength when exposed to electromagnetic radiation at a second excitation wavelength;

e) adding third reporter molecules to said test site, said third reporter molecules comprising guanine conjugated to a third fluorophore, said third fluorophore emitting electromagnetic radiation at a third fluorescence wavelength when exposed to electromagnetic radiation at a third excitation wavelength;

f) adding fourth reporter molecules to said test site, said fourth reporter molecules comprising thymine conjugated to a fourth fluorophore, said fourth fluorophore emitting electromagnetic radiation at a fourth fluorescence wavelength when exposed to electromagnetic radiation at a fourth excitation wavelength;

g) illuminating said test site with electromagnetic radiation at said first excitation wavelength and detecting electromagnetic radiation from said test site with said first pixel;

h) illuminating said test site with electromagnetic radiation at said second excitation wavelength and detecting electromagnetic radiation from said test site with said second pixel;

i) illuminating said test site with electromagnetic radiation at said third excitation wavelength and detecting electromagnetic radiation from said test site with said third pixel; and j) illuminating said test site with electromagnetic radiation at said fourth excitation wavelength and detecting electromagnetic radiation from said test site with said fourth pixel.

7. The method of claim 6, wherein said first pixel has a first filter for blocking said first excitation wavelength and passing said first fluorescence wavelength, said second pixel has a second filter for blocking said second excitation wavelength and passing said second fluorescence wavelength, said third pixel has a third filter for blocking said third excitation wavelength and passing said third fluorescence wavelength, and said fourth pixel has a fourth filter for blocking said fourth excitation wavelength and passing said fourth fluorescence wavelength.

8. A method for monitoring the population of specified molecules at a location as a function of time, said method comprising the steps of:

detecting during a first time interval electromagnetic radiation from said location with at least one pixel of an active pixel sensor to obtain a first measurement;

detecting during a second time interval electromagnetic radiation from said location with said at least one pixel of an active pixel sensor to obtain a second measurement; and comparing said first measurement with said second measurement wherein said location is a test site containing probe molecules, said probe molecules being able to bind with target molecules in a sample to form bound complexes, and wherein said specified molecules comprise bound complexes.

9. The method of claim 8, wherein said specified molecules are luminescent molecules.

10. The method of claim 9, wherein said luminescent molecules are chosen from the group consisting of fluorescent molecules, phosphorescent molecules, chemiluminescent molecules, bioluminescent molecules, electroluminescent molecules, and electro-chemiluminescent molecules.

11. The method of claim 9, wherein said luminescent molecules are fluorescent molecules, said fluorescent molecules absorbing electromagnetic radiation at a first wavelength and emitting electromagnetic radiation at a second wavelength.

12. The method of claim 9, wherein said luminescent molecules are phosphorescent molecules, said phosphorescent molecules absorbing electromagnetic radiation at a first wavelength and emitting electromagnetic radiation at a second wavelength.

13. The method of claim 11 or 12, further comprising illuminating said location with incident electromagnetic radiation, said incident electromagnetic radiation including radiation at a first wavelength.

14. The method of claim 13, further comprising focusing said incident electromagnetic radiation onto said location; and focusing electromagnetic radiation from said location onto said at least one pixel.

15. The method of claim 13, further comprising
filtering said electromagnetic radiation reaching said at least one pixel so as to block said first wavelength and to pass said second wavelength.

16. The method of claim 8, wherein said location is in an amplification chamber, and wherein said specified molecules comprise nucleic acids being amplified in said amplification chamber.

17. The method of claim 8, wherein said location is in a capillary electrophoresis channel.

18. The method of claim 8, wherein said location is in a flow cell.

19. The method of claim 1, wherein said probe molecules are disposed in a gel, such that said bound complexes are arranged in a three-dimensional pattern in said gel.

20. The method of claim 6, wherein said probe molecules are disposed in a gel, such that said bound complexes are arranged in a three-dimensional pattern in said gel.

21. The method of claim 4, wherein said filtering comprises providing a color filter comprising a layer of dyed polyimide resin.

22. The method of claim 7, wherein at least one of said first, second, third and fourth filters comprises a layer of dyed polyimide resin.

23. The method of claim 15, wherein said filtering comprises providing a color filter comprising a layer of dyed polyimide resin.

24. The method of claim 1, further comprising converting said detected electromagnetic radiation to a digital signal.

25. The method of claim 6, further comprising converting said detected electromagnetic radiation to a digital signal.

26. The method of claim 24, further comprising performing data companding on said digital signal.

27. The method of claim 25, further comprising performing data companding on said digital signal.

* * * * *